United States Patent [19]
Tung

[11] Patent Number: 5,437,857
[45] Date of Patent: * Aug. 1, 1995

[54] METHODS AND COMPOSITIONS FOR MINERALIZING AND FLUORIDATING CALCIFIED TISSUES

[75] Inventor: Ming S. Tung, Gaithersburg, Md.

[73] Assignee: American Dental Association Health Foundation, Gaithersburg, Md.

[*] Notice: The portion of the term of this patent subsequent to Dec. 7, 2010 has been disclaimed.

[21] Appl. No.: 104,350

[22] Filed: Aug. 9, 1993

Related U.S. Application Data

[62] Division of Ser. No. 723,839, Jul. 1, 1991, Pat. No. 5,268,167, which is a division of Ser. No. 356,201, May 24, 1989, Pat. No. 5,037,639.

[51] Int. Cl.⁶ .......................... A61K 7/16; A61K 7/18; A61K 9/12
[52] U.S. Cl. .......................... 424/52; 424/48; 424/49; 424/57; 424/602; 106/35; 433/199.1; 433/215; 433/222.1; 433/228.1
[58] Field of Search .................. 433/199.1, 215, 228.1, 433/222.1; 424/49, 52, 57, 602, 48; 106/35

[56] References Cited

U.S. PATENT DOCUMENTS

| | | | |
|---|---|---|---|
| Re. 33,161 | 2/1990 | Brown et al. | 433/199.1 |
| Re. 33,221 | 5/1990 | Brown et al. | 433/199.1 |
| 1,225,362 | 5/1917 | Ruthrauff | 424/48 |
| 2,605,229 | 7/1952 | Marcus | 424/48 |
| 3,679,360 | 7/1972 | Rubin et al. | 424/48 |
| 3,913,229 | 10/1975 | Driskell et al. | 433/215 |
| 3,943,267 | 3/1976 | Randol | 424/49 |
| 4,048,300 | 9/1977 | Tomlinson et al. | 424/52 |
| 4,080,440 | 3/1978 | Diguilio et al. | 424/49 |
| 4,108,980 | 8/1978 | Duff | 424/52 |
| 4,143,128 | 3/1979 | Kim et al. | 424/54 |
| 4,144,324 | 3/1979 | Crutchfield et al. | 424/54 |
| 4,177,258 | 12/1979 | Gaffar et al. | 424/52 |
| 4,183,915 | 1/1980 | Gaffar et al. | 424/52 |
| 4,283,385 | 8/1981 | Dhabhar et al. | 424/52 |
| 4,327,079 | 4/1982 | Aoki | 424/49 |
| 4,342,741 | 8/1982 | Aoki | 424/49 |
| 4,397,837 | 8/1983 | Raaf et al. | 424/52 |
| 4,405,600 | 9/1983 | Besic | 424/57 |
| 4,434,381 | 9/1983 | Gaffar et al. | 424/52 |
| 4,515,770 | 5/1985 | Besic | 424/49 |
| 4,518,430 | 5/1985 | Brown et al. | 433/228.1 |
| 4,532,124 | 7/1985 | Pearce | 424/52 |
| 4,556,561 | 12/1985 | Brown et al. | 424/48 |
| 4,606,912 | 8/1986 | Rudy et al. | 424/52 |
| 4,610,873 | 9/1986 | Rudy et al. | 424/52 |
| 4,612,053 | 9/1986 | Brown et al. | 433/201.1 |
| 4,634,589 | 1/1987 | Scheller | 424/49 |
| 4,672,032 | 6/1987 | Slavkin et al. | 424/52 |
| 4,710,372 | 12/1987 | Scheller | 424/49 |
| 4,714,608 | 12/1987 | Rolla | 424/52 |

(List continued on next page.)

FOREIGN PATENT DOCUMENTS 2570292  3/1986  France .

OTHER PUBLICATIONS

Tung, et al. "Hydrolysis of Dicalcium Phosphate Dihydrate In The Presence Or Absence Of Calcium Fluoride" Basic Biol. Sciences; Dent, J. Res. 64(1): 2–5 Jan., 1985.

(List continued on next page.)

*Primary Examiner*—Ronald W. Griffin
*Attorney, Agent, or Firm*—Banner & Allegretti, Ltd.

[57] ABSTRACT

This invention involves the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds, when applied either onto or into dental tissue prevent and/or repair dental weaknesses such as dental caries, exposed roots and dentin sensitivity. The compounds have the highest solubilities, fastest formation rates and fastest conversion rates (to apatite) among all the calcium phosphorate under physiological conditions. Moreover, in the presence to fluoride the amorphous compound convert rapidly to fluoride containing apatite.

6 Claims, No Drawings

U.S. PATENT DOCUMENTS

| | | | |
|---|---|---|---|
| 4,880,610 | 11/1989 | Constantz | 606/53 |
| 4,908,211 | 3/1990 | Paz | 424/440 |
| 4,923,683 | 5/1990 | Sakuma et al. | 424/52 |
| 5,034,059 | 7/1991 | Constantz | 424/423 |
| 5,037,639 | 8/1991 | Tung | 424/57 |
| 5,047,031 | 9/1991 | Constantz | 606/77 |
| 5,053,212 | 10/1991 | Constantz et al. | 433/199.1 |
| 5,129,905 | 7/1992 | Constantz | 606/76 |
| 5,145,668 | 9/1982 | Chow et al. | 424/52 |
| 5,268,167 | 12/1993 | Tung | 424/52 |

OTHER PUBLICATIONS

Patel, P. R., et al. "Solubiltiy of $CaHPO_4 \times 2H_2O$ In The Quaternary System $Ca(OH)_2$ —$H_3PO_4$ —NaCl–$H_2O$ at 25° C." J. Res. Nat. Bur. Stand.

Brown, W., et al. "Crystallography Of Tetracalcium Phosphate" J. Res. Nat. Bur. Stand. 69A 547–551 (1965).

Moreno, E., et al. "Stability of Dicalcium Phosphate Dihydrate In Aqueous Solutions and Solubility Of Octocalcium Phosphate" Soil Science Society Proceedings, 1960.

McDowell, e tal. "Solubility of $Ca_5(PO_4)_3x$ In The System $Ca(OH)_2$ —$H_3PO_4$ —$H_2O$ at 5, 15, 25 and 37° C." J. Res. Nat. Bur. Stand. 81A 273–281 (1977).

Gregory, T. M. et al. "Solubility of B–$CA_3(PO_4)_2$ In The System $Ca(OH)_2$ –$H_3PO_4$ –$H_2O$ at 5, 15, 25 and 37° C." J. Res. Nat. Bur. Stand. 78A 667–674 (1974).

Gregory, T. M., et al. "Solubility of $CaHPO_4 \times 2H_2O$ in the System $Ca(OH)_2$ –$H_3PO_4$ —$H_2O$ at 5, 15, 25, and 37.5° C.". J. Res. Nat. Bur. Stand 74A 461–475 (1970).

Driskell, et al. "Development of Ceramic and Ceramic Composite Devices For Maxillofacial Applications" J. Biomed. Mater. Res. Symposium; 345–361.

Levine, R. S. et al. "REmineralisation Of Natural Carious Lesions Of Enamel *In Vitro*" Brit. dent. J., 1974; 137, 132 Dental Caries Dental Enamel: Hydroxyapatite: 132–134.

Zimmerman, et al. "The Effect Of Remineralization Fluids On Carious Lesions *In Vitro*" IADR Abstract No. 282 (1979).

Silverstone, et al. "Progressions Of Caries–like Lesions In Vitro After Exposure To Synthetic Calcifying Fluids" IADR Abstract No. 283 (1979).

Wefel, J. S., et al. "Artificial Lesion Formation In $TiF_4$ and APF Treated Enamel" IADR Abstract No. 284 (1979).

Crall, J. J., et al. "Artificial Lesion Formation and Progression after Two–step Topical Fluorides" IADR Abstract No. 285 (1979).

Hiatt, W. H., et al. "Roof Preparation I. Obturation of Dentinal Tubules In Treatment Of Root Hypersensitivity": J. Peridonatal: 373–380 (1972).

Gelhard, T. B. F. M., "Rehardening Of Artificial Enamel Lesions In Vivo" Caries Res. 13: 80–83 (1979).

Silverstone, "Remineralization Phenomena" Caries Res. 11 (Suppl. 1): 59–84 (1977).

Briner, W. W., "Significance Of Enamel Remineralization" 53 239–243 (1974).

NASA And Dentistry, "New Tooth Enamel From Brushite Crystals" (Oct., 1977).

Pickel, F. D. "The Effects Of A Chewing Gum Containing Dicalcium Phosphate On Salivary Calcium And Phosphate" Ala. J. Med: 286–87 (1965).

Trautz, "Crystallographic Studies Of Calcium Carbonate Phosphate" Annals of the N.Y. Acad. Sci. 35, Article 1: 145–160 (1960).

Blumenthal, N. C. et al., "Effect Of Preparation Conditions On The Properties And Transformation Of Amorphous Calcium Phosphate" Mat. Res. Bull. 7: 1181–1190 (1972).

Posner, A. S. et al. "Synthetic Amorphous Calcium Phosphate And Its Relation To Bone Mineral Structure" Accts. Of. Chem. Res. 8 273–281 (1975).

Tung, M. S., et al. "An Intermediate State In Hydrolysis Of Amorphous Calcium Phosphate" Calcif Tissue Int. 783–790 (1983).

LaGeros, R. Z., "Apatitic Calcium Phosphates: Possible Dental Restorative Materials" IADR Abstract No. 1482 J. Dent. Res. 61 (1982).

Tung, M. S., et al. "The Effects of Calcium Phosphate Solutions on Permeability of Dentin" J. Dent. Res., 65 Abstract No. 167 (1986).

Brown, et al., "Singular Points in the Chemistry of Teeth," IADR Abstract No. 120, J. Dent. Res. 54:74 (1975).

Guide To Dental Materials And Devices, 7 Ed. p. 49 (ADA 1974).

Ababa Takaaki, et al. "Small–Angle X–Ray Scattering Study On The Transformation Of Amorphous Calcium Phosphate To Crystalline Apatite," Chem. Abstracts, vol. 91 No. 13, Abstract No. 105934q (1979).

(List continued on next page.)

OTHER PUBLICATIONS

Ababa Takaaki, "X-Ray Diffraction Study On The Amorphous And Crystalline Components in Bone Mineral" Chem. Abstracts, vol. 91, No. 13, Abstract No. 1 (1979).

Termine, John D., et a. "Calcium Phosphate In Vitro" Chem. Abst. vol. 73 Abstract No. 126985a (1970).

Hong, Y. C., et al. (1989): "The Periapical Tissue Reactions To A Calcium Phosphate Cement In The Teeth Of Monkeys", J. Dent. Res. (submitted).

McDowell, et al., "Solubility Study Of Calcium Hydrogen Phosphate. Ion-Pair Formation," Inorg. Chem. 10:1638–1643 (1971).

Tung, et al. "Effects of Calcium Phosphate Solutions on Dentin Permeability" vol. 19 No. 8, J. of Endodontic (1983).

Brown, "Solubilities of Phosphates and Other Sparingly Soluble Compounds" from Griffith, et al., Environmental Phosphorous Handbook (John Wiley & Sons New York 1973).

DeRijk, et al. (1986) "Clinical Evaluation of an Hydroxyapatite Precipitate for the Treatment of Dentinal Hypersensitivity" Biomedical Engineering V. Recent Developments, Proc of 5th Southern Biomedical Engineering Conference, Subrate Saha, Ed., New York: Pergamon Press, pp. 336–339.

Lu, et al., (1988) "New Attachment Following the Use of Novel Calcium Phosphate System" J. Dent. Res. 67:352, Abst. No. 1913.

Schreiber, et al. (1988) "Remineralization of Root Caries Lesion by a Calcium Phosphate Slurry," J. Dent. Res. 67:Abst. No. 255.

Sugawara, et al. (1987) "A Calcium Phosphate Root Canal Sealer–Filler" J. Dent. Res. 66:296 Abst. No. 1516.

Sugawara et al. (1988) "Formation of Hydroxyapatite in Hydrogels from Tetracalcium Phosphate/Dicalcium Phosphate Mixtures," J. Dent. Res. (submitted).

Matsuya et al. "Effects of pH on the Reactions of Tetracalcium Phosphate and Dicalcium Phosphate" IADR Abstracts 1991.

Tamotsu et al. "Synthesis and Characteristics of Amorphous Calcium Carbonate in Ethanol" Chem. Sb. vol. 103, No. 18 (1985).

METHODS AND COMPOSITIONS FOR MINERALIZING AND FLUORIDATING CALCIFIED TISSUES

This invention was made in the course of research, supported partially by the Government under Grant DE 08916, awarded by the National Institute of Dental Research. The Government may have certain rights in the invention.

This is a divisional of application Ser. No. 07/723,839 filed Jul. 1, 1991, now U.S. Pat. No. 5,268,167, which is a divisional of application Ser. No. 07/356,201 filed May 24, 1989, now U.S. Pat. No. 5,037,639.

BACKGROUND OF THE INVENTION

1. Field of the Invention

This invention relates to certain amorphous calcium compounds that are unique in their applications as remineralizers of caries lesions, cavities and root erosions of the tooth. These amorphous compounds when further containing a fluoride compound can also be used for topical fluoridation of the teeth. When used for either fluoridation or mineralization these compounds prevent further tooth decay and dentin sensitivity and may actually restore the lesions caused by dental caries.

2. Description of the Prior Art

When an incipient lesion or cavity develops on the surface of a tooth, the dentist traditionally fills the cavity that forms. This procedure may prevent the decay from spreading further, but does not restore the tooth to its original state. A considerable amount of research, however, has recently been directed toward the remineralization dental lesions. The object of this remineralization has been the deposit of hydroxyapatite, $Ca_5(PO_4)OH$, upon the surface of the tooth. Through this remineralization process further tooth decay is prevented and the tooth is restored to its original form.

In the area of remineralization of dental tissue there have been at least three approaches. One approach uses a metastable fluoride containing calcium phosphate solution supersaturated with respect to fluorapatite and hydroxyapatite which will form apatite slowly when applied. A second method uses combinations of sparingly soluble calcium phosphates with crystallized tetracalcium phosphate and at least one different calcium phosphate in slurries or paste forms. Such an application is disclosed in U.S. Pat. No. 1,612,053 issued to Brown et al. Yet a third method uses potassium oxalate solutions to obturate the dental tubulus as disclosed in U.S. Pat. No. 4,538,990 issued to Pashley and U.S. Pat. No. 4,057,621 issued to Pashley et al.

These prior art methods are characterized by several practical problems. When a supersaturated solution using a single calcium phosphate is used, the remineralization process is extremely slow. The remineralization process is in fact so slow that an inconvenient amount of time is required for its completion. Another problem with the prior art methods is that as the apatite is deposited upon the teeth, the pH's of the treating solutions change. Such a change can make the solution either too acidic or too alkaline, creating the possibility of damaging the dental tissue.

Therefore, there remains a need for a treatment which achieves rapid remineralization of teeth similar to the natural process of biological mineralization, without the dissolution of the existing dental tissue.

In the area of topical fluoridation of the dental tissue there has also been at least three approaches. The first approach introduces simple fluoride containing compounds onto the surface of the dental enamel. This process relies upon the fluoride migrating through the enamel and strengthening the teeth. The second approach introduces a acidulated phosphate fluoride, which involves the dissolution of some of the dental tissue and precipitation of the calcium fluoride. The third approach involves an intermediate product of dicalcium phosphate dihydrate which is then converted to fluorapatite and precipitated upon the teeth. The first fluoridation method is slow and requires a long period of time in which to achieve adequate fluoridation of the dental tissue. The last two methods involve the dissolution of the existing enamel. There remains a need for a method in which fluoridation can be achieved rapidly and without damage to the teeth.

Although the prior art does not teach the use of amorphous calcium compounds for remineralization of teeth, it does refer to amorphous calcium phosphate as an aspect of the investigation of natural bone formation. See *Synthetic Amorphous Calcium Phosphate and Its Relation to Bone Mineral Structure*, Posner and Betts, ACCOUNTS OF CHEMICAL RESEARCH, Jan. 31, 1975; *An Intermediate State in Hydrolysis of Amorphous Calcium Phosphate*, Tung and Brown, CALCIFIED TISSUE INTERNATIONAL, 1983. However, these studies of amorphous calcium phosphate as a precursor of bone do not involve the use of the compound and are significantly different from the present invention. Bone tissue is 50% organic material and 50% inorganic material, whereas dental tissue is 90% inorganic. As such, significantly different factors affect the different tissues.

The prior art further teaches the use of amorphous tricalcium phosphate as a component of the surgical cement in teeth and bones. See U.S. Pat. No. 4,684,673 issued to Adachi. Contrary to the present invention, Adachi teaches a filler or a cement, not a composition which reconstructs the dental tissue.

SUMMARY OF THE INVENTION

The potential for application of dental remineralization is vast. Dentists fill millions of cavities each year. If these cavities where remineralized rather than filled the general dental health of the public would be increased substantially since remineralization results in a whole tooth. The present invention seeks to provide a remineralization compositions and methods that can practically be applied under a dentists care and reduce the need for filling of the teeth.

This invention involves the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds, when applied either onto or into dental tissue prevent and/or repair dental weaknesses such as dental caries, exposed roots and dentin sensitivity. The compounds have the highest solubilities, fastest formation rates and fastest conversion rates (to apatite) among all the calcium phosphate under physiological conditions. Moreover, in the presence of fluoride the amorphous compound convert rapidly to fluoride containing apatite.

The advantages of the use of the amorphous compounds according to the present invention as compared to the solutions and slurries of the prior art are many. Most importantly, the use of the compounds and methods of the invention allows for the most rapid deposition of mineral upon dental tissues. Therefore, remineralization of the teeth can be achieved more quickly. In addition, the present invention provides for remineralization and refluoridation simultaneously when the amorphous calcium compound contains a fluoride.

Another significant advantage is that the present invention will not damage the teeth because there is no dissolution of the existing dental tissue and no significant decrease in pH of the solution during the remineralization process.

Yet another advantage of the present invention is that it provides compositions and methods which can practically be used in remineralization without long term or excessive repeated treatment.

Yet a further advantage of the present invention is the provision of a composition for remineralization of teeth which can be easily formulated and easily applied to the teeth.

Thus, the present invention provides compositions and methods for remineralization of caries lesions that are practical for the use in a clinic or a household environment. The invention also provides compositions and methods for the rapid fluoridation of teeth by the use of amorphous calcium fluoride compounds. Through either of these processes damaged dental tissues can be quickly and easily repaired, restoring the tooth to a whole healthy tooth.

Further objects of the inventions will become apparent with the following description of the preferred embodiments and claims.

DETAILED DESCRIPTION OF THE PREFERRED EMBODIMENTS

The inventor has found that ACP, ACPF, and ACCP are solid solutions with variable compositions. These solutions have no long range structure; however, they are homogeneous when measured on an angstrom scale. Under physiological conditions these amorphous calcium compounds have high solubilities, high formation rates and high rates of conversion to apatite. The high rates of formation and conversion allow the remineralization of the dental tissue to take place at a greater speed. This speed allows for a practical method for remineralization of dental tissue without an undue number of treatments. Moreover, in the presence of fluoride, the amorphous compounds convert to fluoride-containing apatite.

Remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established, the amorphous compound is deposited on and into the tooth. Once deposited on the dental tissue the mineral will recrystallize in situ and reform the tooth.

In another embodiment of the invention, calcium phosphate compounds including amorphous calcium phosphate compounds are formed on and into the tooth, in situ, as an intermediate prior to the crystallization of the apatite. Such an embodiment includes carbonated solutions containing calcium ions, fluoride ions, carbonate ions and phosphate ions, maintained under a pressurized carbon dioxide atmosphere. The solution also preferably contains a cariostatic agent, a stabilizing agent, and an adhesion enhancing and dentin tubule obstructing agent. Under the pressurized carbon dioxide atmosphere, the solutions have a lower pH and are stable. When applied under oral conditions, carbon dioxide escapes, causing the pH to increase. This increase in pH results in a supersaturated solution and ultimately rapid precipitation of calcium phosphate compounds such as ACP, ACPF and ACCP. Specifically, the ACP, ACPF, or ACCP precipitate on and into the dental tissue due to the increase in instability of the solution. The precipitation rate increases as temperature and pH of the solution increases. The amorphous calcium compounds then crystalize to form apatite.

The pH and degree of supersaturation (with respect to amorphous tricalcium phosphate) of an aqueous solution containing 16 mM of calcium chloride 0.6 mM of potassium phosphate and 0.1 mM of potassium fluoride is shown before and after application in Table 1 (below). Before application, the composition was held under a carbon dioxide pressure of 1.5 atmospheres and at a temperature of 4° C.; after application, the composition was under normal atmospheric pressure (0–0.01 atm of carbon dioxide) and a temperature of 35° C.

TABLE 1

The pH and degree of supersaturation (with respect to amorphous tricalcium phosphate) of the solution before and after application.

| | Temp. °C. | pH | $CO_2$ Pressure (atm) | Total Carbon (mM) | Degree of Saturation |
|---|---|---|---|---|---|
| Before | 4 | 4.5 | 1.5 | 111 | under-saturation |
| After | 37 | 10.0 | 0 | 0 | $10^{5.0}$ |
| | | 7.75 | 0.005 | 5.69 | $10^{3.1}$ |
| | | 7.5 | 0.01 | 6.44 | $10^{2.6}$ |

The driving forces behind the precipitation of the amorphous calcium compound from the above aqueous solutions are the temperature and the pH. The solutions can maintain higher calcium and phosphate concentrations at a lower pH and a lower temperature. Therefore as the pH and the temperature rise the solutions become supersutured. In this supersaturated state the solutions can rapidly precipitate amorphous calcium compounds onto a tooth.

Another feature of the invention is its capacity to fluoridate the dental tissue. When the amorphous calcium compounds exist in the presence of fluoride ions, fluoride containing apatite is precipitated. The beneficial effects of fluoride in dental tissue are well known.

This invention provides the compositions that contain or form ACP, ACPF, ACCP and methods that deposit the ACP, ACPF, or ACCP on and into the tooth. The compositions are ACP, ACPF, ACCP themselves or solutions containing calcium, fluoride, carbonate and phosphate that will form ACP, ACPF, or ACCP when applied. Upon application, ACP, ACPF, or ACCP remineralize and/or fluoridate the tooth and, in the case of exposed root and dentin sensitivity, obstruct the dentinal tubules. Thus use of the compositions in accord with this invention provides relief to damaged dental tissues.

The following examples serve to illustrate preparation and use of the compositions of the present invention.

EXAMPLE 1

A gel, solution, or powder containing an amorphous calcium compound (such as ACP, ACPF, or ACCP) alone or together with other beneficial ingredients such as fluoride was applied on the tooth surface. The ACP, ACPF, or ACCP was prepared in two ways: (1) ACP, ACPF or ACCP powder was first prepared by rapid mixing of calcium and phosphate solutions (with or without fluoride ions or carbonate ions) at high pH (>9.9) and high concentration (0.1M to 2M), the resultant mixture was then filtered and dried to form a powder; the ACP, ACPF, or ACCP powder was then suspended in the solution or gel; or (2) Rapid mixing of two solutions, one containing a high concentration of calcium ion such as 1.5M $Ca(NO_3)_2$, the other containing a high concentration of phosphate such as 1.5M $K_2HPO_4$ with or without fluoride ions or carbonate ions, produced ACP, ACPF or ACCP in gel form.

EXAMPLE 2

A solution, slurry, or gel containing a high concentration of phosphate (such as 0.1M to 2M $K_2HPO_4$) with high pH ($\geq 9$) and 1000 ppm fluoride was applied to the tooth surface for 1 min., followed by application of a solution or gel containing a high concentration of calcium ions (such as 0.1M to 2M $Ca(NO_3)_2$). The combination of the two solutions result in the formation of amorphous calcium compounds. The amorphous calcium compounds deposited upon the tooth then convert to fluoride containing apatite in situ.

EXAMPLE 3

A carbonated cold solution, foam, or gel (5° C. and under pressurized carbon dioxide atmosphere) is prepared containing a high concentration of calcium, (40 mM) and phosphate (27 mM). The solution also contains cariostatic agents, such as strontium and tin ions, an adhesive enhancing agents, such as oxalate, aluminum and/or ferric ions, and stabilizing agents such as macromolecules (polylysine or carboxymethyl cellulose) and/or hydroxyethane diphosphonate. The solution is then applied on the tooth surface. The carbon dioxide escapes from the solution under oral atmosphere and the pH of the solution increases. As ions diffuse into the tooth and into a milieu of higher temperature, they leave behind the stabilizing agents. This results in an increasingly unstable solution and rapid precipitation.

The carbonated cold solution or gel may also be prepared by mixing two cold solutions under carbon dioxide atmosphere just before the application. One solution containing calcium and other beneficial cations and ingredients, and the other solution containing phosphate, fluoride and other beneficial anions and ingredients.

EXAMPLE 4

Chewing gum is prepared containing ACP, ACPF or ACCP as prepared in example 1, with or without fluoride.

EXAMPLE 5

Solid powders containing mixtures of calcium salts and phosphate salts with or without fluoride or carbonate salts such as 3 mM calcium chloride, 2 mM sodium phosphate and 0.5 mM sodium fluoride, are applied directly to the tooth, used as pumice flour, or dispersed in gel, chewing gum or other nonaqueous mediums such as toothpaste which is placed in contact with the tooth. These powders are easily dissolved in saliva and then reprecipitated as ACP, ACPF or ACCP in and on the tooth.

EXAMPLE 6

A carbonated beverage or mouth rinse contains calcium ions, phosphate ions, and other ingredients which form ACP, ACPF, or ACCP in conditions simulating the oral cavity.

The preferred embodiment of the present invention is now fully described. The above description, however, is only illustrative of the invention and is not intended to limit the invention in spirit or scope. Only the following claims and their equivalents limit the scope of the invention.

I claim:
1. A dental restorative comprising in combination:
   a substantially non-aqueous, non-toxic carrier capable of suspension of amorphous calcium compounds or a material that will form amorphous calcium compounds therein; and
   a material comprising or that will form amorphous calcium phosphate, amorphous calcium phosphate fluoride or amorphous calcium carbonate phosphate suspended within said carrier;
   whereby when the combination is contacted with the teeth, a calcium phosphate compound is deposited and apatite is formed on and in the teeth.
2. A method for treating teeth comprising contacting the dental restorative of claim 1 with the teeth.
3. A dental restorative comprising a substantially aqueous slurry containing amorphous calcium phosphate fluoride; whereby when applied to a tooth the slurry precipitates a calcium phosphate fluoride compound on and into the tooth, said calcium phosphate fluoride then forming fluoride containing apatite.
4. A method for treating teeth comprising contacting the dental restorative of claim 3 with the teeth.
5. A dental restorative comprising a substantially aqueous slurry containing amorphous calcium carbonate phosphate; whereby when applied to a tooth the slurry precipitates a calcium carbonate phosphate compound on and into the tooth, said calcium carbonate phosphate then forming apatite.
6. A method for treating teeth comprising contacting the dental restorative of claim 5 with the teeth.

* * * * *

EX PARTE REEXAMINATION CERTIFICATE (5062nd)

United States Patent
Tung

(10) Number: US 5,437,857 C1
(45) Certificate Issued: *Feb. 15, 2005

(54) METHODS AND COMPOSITIONS FOR MINERALIZING AND FLUORIDATING CALCIFIED TISSUES

(75) Inventor: Ming S. Tung, Gaithersburg, MD (US)

(73) Assignee: American Dental Association Health Foundation

Reexamination Request:
No. 90/006,323, Jul. 8, 2002

Reexamination Certificate for:
Patent No.: 5,437,857
Issued: Aug. 1, 1995
Appl. No.: 08/104,350
Filed: Aug. 9, 1993

(*) Notice: This patent is subject to a terminal disclaimer.

Related U.S. Application Data

(62) Division of application No. 07/723,839, filed on Jul. 1, 1991, now Pat. No. 5,268,167, which is a division of application No. 07/356,201, filed on May 24, 1989, now Pat. No. 5,037,639.

(51) Int. Cl.$^7$ ............ A61K 9/68; A61K 7/16; A61K 33/42; A61C 5/00
(52) U.S. Cl. ............ 424/52; 424/48; 424/49; 424/57; 424/602; 106/35; 433/199.1; 433/215; 433/222.1; 433/228.1
(58) Field of Search ............ 424/52, 43, 44, 424/57, 48, 49, 601, 602, 606; 514/901

(56) References Cited

U.S. PATENT DOCUMENTS 3,679,360 A   7/1972   Rubin et al.
5,037,639 A   8/1991   Tung

OTHER PUBLICATIONS

J.D. Termine and E.D. Eanes, "*Comparative Chemistry of Amorphous and and Apatite Calcium Phosphate Preparations*," Cacl. Tiss. Res. vol. 10, pp. 171–187 (1972).

A.L. Boskey and A.S. Posner, "*Conversion of Amorphous Calcium Phosphate to Microcrystalline Hydroxyapatite, A pH–Dependent, Solution–Mediated, Solid–Solid Conversion*," The Journal of Physical Chemistry, vol. 77, No. 19, pp. 2313–2317 (1973).

R.Z. LeGeros, "*Calcium Phosphates in Oral Biology and Medicine*," Monographs in Oral Science, vol. 15, pp. 66–71 (1991).

M.S. Tung, et al., "*The Effects of Calcium Phosphate Solutions on Permeability of Dentin*," J. Dent. Res., 65 Abstract No. 167 (1986).

*Primary Examiner*—Christopher S. F. Low

(57) ABSTRACT

This invention involves the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds, when applied either onto or into dental tissue prevent and/or repair dental weaknesses such as dental caries, exposed roots and dentin sensitivity. The compounds have the highest solubilities, fastest formation rates and fastest conversion rates (to apatite) among all the calcium phosphorate under physiological conditions. Moreover, in the presence to fluoride the amorphous compound convert rapidly to fluoride containing apatite.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

\* \* \* \* \*